United States Patent [19]

Picciola et al.

[11] Patent Number: 4,791,104

[45] Date of Patent: Dec. 13, 1988

[54] DIHYDROBENZOTHIOPHENE AND THIOCHROMANE AMINOALCOHOLS

[75] Inventors: Giampaolo Picciola, Milan; Mario Riva, Monza; PierGiuseppe De Meglio, Milan; Piergiorgio Gentili, Treviglio, all of Italy

[73] Assignee: Maggioni-Winthrop S.p.A., Milan, Italy

[21] Appl. No.: 940,090

[22] Filed: Dec. 10, 1986

[30] Foreign Application Priority Data

Jun. 25, 1986 [GB] United Kingdom ............... 8615562

[51] Int. Cl.$^4$ .................. A61K 31/70; C07D 409/02; C07D 295/02; C07D 409/14
[52] U.S. Cl. ........................ 514/58; 544/376; 544/386; 546/199; 546/201; 546/202; 536/46; 536/103; 514/252; 514/324
[58] Field of Search ............... 544/376, 386; 546/199, 546/201, 202; 536/46, 103; 514/58, 252, 324

[56] References Cited

U.S. PATENT DOCUMENTS

| | | | |
|---|---|---|---|
| 3,928,358 | 12/1975 | Renth | 544/377 |
| 4,251,526 | 2/1981 | McCall | 544/376 X |
| 4,447,620 | 5/1984 | Sih et al. | 544/376 X |
| 4,638,070 | 1/1987 | Lambelin et al. | 549/23 |

FOREIGN PATENT DOCUMENTS 53-005178 1/1978 Japan .................. 544/376
53-082788 7/1978 Japan .................. 544/376

Primary Examiner—Teddy S. Gron
Assistant Examiner—Virginia Caress
Attorney, Agent, or Firm—Oblon, Fisher, Spivak, McClelland & Maier

[57] ABSTRACT

The invention is concerned with dihydrobenzothiophene and thiochromane derivatives of the generic formula

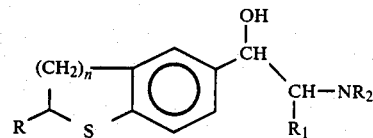

The compounds show anti-hypertensive, platelet aggregation inhibiting, hypolipemic, antianoxic spasmolytic, anthithrombotic, calcium antagonizing and neuroleptic activity.

9 Claims, No Drawings

DIHYDROBENZOTHIOPHENE AND THIOCHROMANE AMINOALCOHOLS

This invention is concerned with new pharmacologically active compounds. More particularly, the compounds with which this invention is concerned are dihydrobenzothiophene and thiochromane aminoalcohols of the formula

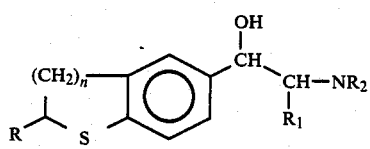

wherein R and $R_1$ represent hydrogen or a lower alkyl group, n represents an integer selected from 1 and 2, and $R_2$ represents a divalent radical selected from (a)

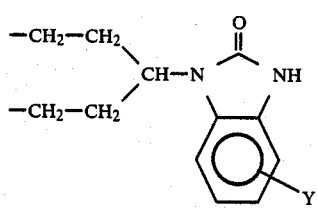

wherein Y represents hydrogen or halogen;

(b)

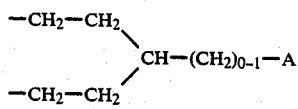

wherein A is a group selected from

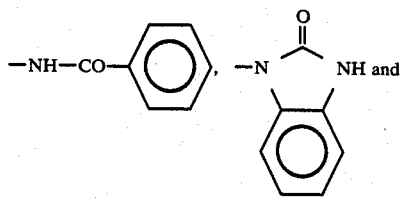

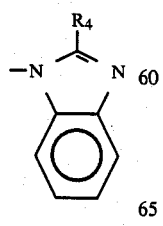

wherein $R_4$ represents a lower alkyl group;

(c)

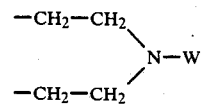

and (d)

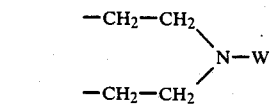

wherein W represents hydrogen, a 2-furoyl radical or a group

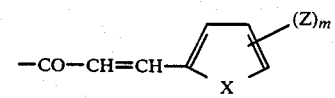

wherein X represents a group selected from —CH=CH—, —O— and —S—, Z represents a hydrogen, halogen or a lower alkyl or alkoxy group and m is an integer from 1 to 3, and their salts with inorganic acids, organic acids, cationic exchange resins and complexes with cyclodextrins.

As apparent to all those having knowledge of organic chemistry, the compounds of formula I in which $R_1$ does not represent hydrogen possess two structural asymmetry centers at the carbon atoms of the aliphatic side chain to which the hydroxy and the basic nitrogenated group are attached. The compounds may therefore exist in threo and erythro stereoisomeric forms. In many cases, by the manufacturing processes which will be hereinafter described, a mixture of the two stereoisomeric forms is formed as a result of the reaction, and it will be necessary to carry out an appropriate separation in order to get the desired form in a satisfactory pure condition.

The process for preparing the compounds of the foregoing formula I consists in reacting approximately equimolecular amounts of an alpha haloketone of formula II and a secondary amine of formula III, preferably in the presence of a proton acceptor in a solvent, thus obtaining the amino ketone of formula IV. This latter is eventually hydrogenated to give compound I, either as a mixture of threo and erythro steroisomers, or as one single steroisomer, depending on the selected reaction conditions. If a mixture of diastereoisomers is obtained, then a separation into the two steric forms will have to be carried out in order to get them in a pure condition.

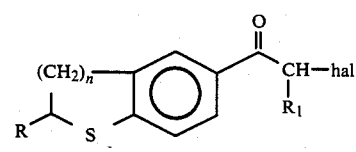

HNR$_2$       III

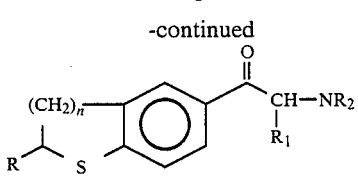

It is understood that the symbols R, $R_1$, $R_2$ and n have, in all the formulas II, III and IV, the same signification indicated above for formula I.

The reaction between compounds II and III is best carried out in a solvent of the classes comprising lower aliphatic alkanols, such as methanol, ethanol, propanol, isopropanol, butanol and the like; lower aliphatic ketones, such as acetone, methyl ethyl ketone and the like; acetonitrile; di-lower alkyl-formamides, such as dimethylformamide; aromatic hydrocarbons such as benzene, toluene, xylene and the like.

The reaction temperature is usually between the room temperature and the boiling temperature of the solvent.

The proton acceptor in the reaction between compound II and III may be any basic substance not interfering with the reaction. Preferably, inorganic substances are employed, most commonly alkali and alkaline earth carbonates and bicarbonates. Particularly effective were found to be sodium carbonate and sodium bicarbonate. However, also tertiary amines may be useful, and in some instances an excess of the amine III may give practical results.

The reaction time may range between wide limits. It has been found that a reaction time between 6 and 30 hours is appropriate, with limits between 6 and 24 hours being preferred.

Hydrogenation of compound IV to give the compounds of the present invention is best effected using a metal hydride, such as sodium borohydride or lithium aluminum hydride, in a solvent not interfering with the hydride and generally with the hydrogenation reaction. The temperature may range between about −15° and 20°, preferably between about 0° C. and 10° C., during the addition of the hydrogenating agent. The same temperature limits may be used if it is preferred to add a solution of the amino ketone to the hydrogenating agent dissolved or suspended in an appropriate solvent. At the end of the addition the reaction mixture is kept for some time, preferably 2–6 hours, at a temperature ranging between the room temperature and the boiling temperature of the solvent.

In many instances it has been found that it is convenient to carry out the hydrogenation step on the reaction mixture resulting from the reaction between compounds II and III, without the necessity of isolating the amino ketone IV.

As above stated, the above disclosed reactions normally, although not necessarily, cause formation of two diastereoisomeric forms of the compounds, due to the presence of two asymmetry centers in their molecule. Any known process for separating the diastereoisomeric forms from each other may be employed, such as fractional crystallization from an appropriate solvent to be selected depending on the solubility properties of the two forms. On the other hand, one of the forms may precipitate from the reaction solvent at the end of the hydrogenation step, the other remaining dissolved being in turn precipitated from the solvent, after filtering off the solids, by the addition of a hydrogen halide, such as hydrogen chloride, to the solvent, and isolating the diastereoisomeric form as the hydrohalogenide, usually the hydrochloride or the hydrobromide. Another common separation technique is chromatography, particularly dry column chromatography.

The products of this invention, both those of the formulas I and IV above, show anti-hypertensive, platelet aggregation inhibiting, antithrombotic, hypolipemic, antianoxic, spasmolytic, calcium antagonizing and neuroleptic activity.

The anti-hypertensive activity was tested on groups of 5 SH rats (spontaneously hypertensive rats) and 5 DOCA rats (deoxycorticosterone acetate and sodium chloride loaded rats) weighing 200±10 g, fasting from 18 hrs and treated orally with the invention compounds suspended in 0.5% gum arabic.

Changes in blood pressure (mm Hg) before (T=0) and after treatment (2, 4 and 6 hrs) were measured according to the method of tail artery plethysmography reported in "Spontaneously hypertensive rats (SHR), guidelines for breeding, care and use", SHR Conference, 1976, page 11.

The heart rate was also tested (BP Recorder No. 8006 supplied by Basile, Comerio, Italy). The arterial pressure before the treatment was 210±10 mmHg.

Table 1 shows that the tested compounds are endowed with good anti-hypertensive activity at all tested doses.

The peak effect was noted 2–4 hrs after the treatment and the duration of the effect was more than 6 hrs: in this period no remarkable increase of heart rate was registered. At the dosis of 5 mg/kg all tabulated compounds display an anti-hypertensive effect higher than Tibalosine. Two of them (MG 16302 and MG 16444) at the dosis of 1 mg/kg per os are even more active than Urapidil.

TABLE 1

| Compound | Max. changes in systolic pressure (mmHg) SHR | | |
|---|---|---|---|
| | 15 | 5 | 1 mg/kg po |
| MG 16302 | −48 | −48.6 | −36.2 |
| MG 16294 | −48 | −30.0 | −12.8 |
| MG 16444 | −47.5 | −47.0 | −28.2 |
| MG 16287 | −44.3 | −25.7 | −25 |
| MG 16310 | −34.9 | −24.6 | — |
| MG 16411 | −41.7 | −32.7 | −15.2 |
| Tibalosine | −67 | −13.2 | ~0 |
| Urapidil | −72.4 | −47 | −16 |

To test the antagonism against phenylephrine (PHE) induced hypertension, male rats CrI:CD (SD)BR were anesthesized with urethane, 1 g/kg i.p. of PHE was administered cumulatively and dose-response curves were obtained (controls). Dose-response curves were similarly obtained after administration of the test drugs (1 mg/kg i.v.). From the two curves the PHE dosis causing a 50 mm Hg increase of the arterial pressure was calculated. The PHE dosis was about 3–6 times, in comparison with the controls, after administration of MG 16445, 16287, 16302, 16444, 16310, and about 17 times after MG 16311.

The protection against toxic adrenaline doses was tested as follows. Groups of 10–20 male mice CrI:CD 1(CR) BR were treated orally with vehicle (controls) and with various doses of the compounds. After 2 hrs 14.5 mg/kg of l-adrenaline was administered intraperitoneally and mortality was recorded after 24 hrs; in controls mortality was 100%. From log-dose-% protection curves the 50% protective doses were calculated (Litchfield et al., J. Pharmacol. Exp. Ther. 96, 99, 1949).

Table 2 gives the results obtained with some of the compounds as compared with known drugs. The new compounds generally show an activity higher than Tibalosine and Fentolamine. MG 16311 was equivalent to Prazosin.

TABLE 2

| Compound | PD$_{50}$ mg/kg po | Fid. limits (P = 0,05) |
|---|---|---|
| MG 16270 | 5.5 | 4.0–7.5 |
| MG 16278 | 12.0 | 9.16–15.7 |
| MG 16290 | 7.2 | 4.41–11.76 |
| MG 16287 | 2.0 | 1.55–2.59 |
| MG 16299 | 6.2 | 3.9–9.8 |
| MG 16298 | 2.75 | 1.85–4.08 |
| MG 16302 | 5.75 | 3.6–9.2 |
| MG 16318 | 8.1 | 5.88–11.15 |
| MG 16311 | 0.59 | 0.46–0.79 |
| MG 16317 | 4.7 | 3.69–5.98 |
| MG 16310 | 1.2 | 0.80–1.79 |
| MG 16413 | 8.4 | 6.88–10.25 |
| MG 16410 | 6.0 | 4.97–7.25 |
| MG 16443 | 4.9 | 3.4–7.05 |
| MG 16444 | 8.0 | 6.0–10.7 |
| MG 16445 | 8.1 | 6.2–10.6 |
| Prazosin | 0.70 | 0.59–0.83 |
| Tibalosine | 5.5 | 3.36–8.99 |
| Phentolamine | 8.0 | 6.3–10.15 |

The receptor binding assay for the inhibition of $^3$H-Prazosin, $^3$H-Clonidine and $^3$H-Spiperone binding to rat brain membrane was carried out according to Greenberg et al., Life Sci. 19, 69, 1976, and U'Prichard et al., Molec. Pharmacol. 13, 454, 1977.

Data for the tested compounds are reported in Table 3 where the 50% inhibiting concentrations (IC$_{50}$) of Tibalosine and Urapidil are also given. The invention compounds show a good affinity toward alpha$_1$-adrenergic receptors, comparable with or higher than the two comparison substances, and poor or no affinity toward alpha$_2$-adrenergic receptors.

A moderate affinity toward serotoninergic$_2$(5-HT$_2$) factors is displayed by MG 16302.

TABLE 3

| Compound | Concentration (M) | % Inhibition of the specific binding | | |
|---|---|---|---|---|
| | | $^3$H—Prazosin ($\alpha_1$) | $^3$H—Clonidine ($\alpha_2$) | $^3$H—Spiperone (5-HT$_2$) |
| MG 16294 | 5.4 × 10$^{-7}$ | 47 | 7.5 | 16.0 |
| | 5.4 × 10$^{-6}$ | 90.0 | 3.5 | 47.0 |
| | 1.08 × 10$^{-4}$ | 99.5 | 20.0 | 73.4 |
| MG 16302 | 5.4 × 10$^{-7}$ | 93.0 | 0 | 31.5 |
| | 5.4 × 10$^{-6}$ | 99.0 | 4.8 | 80.0 |
| | 1.08 × 10$^{-4}$ | 100 | 40.0 | 100 |
| Tibalosine | IC$_{50}$ (a) | 4 × 10$^{-7}$ | 1 × 10$^{-3}$ | — |
| Urapidil | IC$_{50}$ (b) | 8 × 10$^{-7}$ | 1.4 × 10$^{-5}$ | — |

(a) Qian J. H. et al. - Arch. int. Pharmacodyn 266, 264; 1983
(b) Van Zwieten P. A. et al. - Arch. int. Pharmacodyn. 276, 180; 1985

The effect on platelet aggregation was tested ex vivo according to the method of Minsker (J. Pharmacol. Exp. Ther. 210, 37, 1979) slightly modified. Groups of 3 rats (280–350 g) were treated orally with vehicle (controls) and compounds (0.15 mM/kg). Blood was collected and pooled from rats of each group 1 hr after treatment and the platelet rich plasma (PRP) was separated by centrifugation.

Platelet aggregation was stimulated with collagen (2–4 mcg/ml) added simultaneously to PRP of control and treated rats. The results were assessed photometrically. Each test was replicated 4 times in groups of 3 animals. Aggregation curves were evaluated in terms of two parameters namely maximum optical density variation (maximum aggregation) and aggregation rate.

Table 4 gives the effects recorded after treatment with some of the tested compounds. They show an activity comparable to Ticlopidine and Suloctidil and only slightly lower than Dipiridamol.

TABLE 4

| COMPOUND | Inhibition | |
|---|---|---|
| | Maximum aggregation | Aggregation rate |
| MG 16298 | −70 | −70 |
| MG 16304 | −63.7 | −75.1 |
| MG 16305 | −62.4 | −62.0 |
| MG 16309 | −67.0 | −68.4 |
| MG 16313 | −75.0 | −81.0 |
| MG 16315 | −57.2 | −56.6 |
| MG 16375 | −51.9 | −50.0 |
| MG 16403 | −62.2 | −55.3 |
| MG 16444 | −64.7 | −68.0 |
| TICLOPIDINE | −70.0 | −56.0 |
| SULFINPYRAZONE | −92.5 | −89.0 |
| SULOCTIDIL | −69.0 | −57.5 |

Sprague Dawley Nos male rats (180–200 g) were treated orally for 4 consecutive days with vehicle (0.5 ml/100 g gum arabic 2.5%, controls) and with 1–2 doses of the tested compounds, and were sacrificed at the 5th day after 18 hrs fasting. Total cholesterol (CHOL), triglycerides (TG), HDL cholesterol (CHOL-HDL) were assayed in serum and the liver was weighed.

Table 5 gives the obtained results. MG 16444 and MG 16445 cause a dose-dependant, marked decrease both of CHOL and TG while MG 16311, MG 16426 and MG 16448 decrease TG and increase CHOL-HDL. Except for MG 16426, the liver weight is not affected. Their activity is higher than Clofibrate which, as known, causes a significative liver increase. The Probucol activity is moderate and is noted only after prolonged treatment (8 days).

MG 16311 and MG 16426 decrease the hyperlipemic effect caused by Triton WR 1339 (Moss et al., Antihyperlipidemic agents, from "Screening Methods in Pharmacology", Vol. II, page 136, Academic Press, 1971) lowering serum levels of CHOL and TG.

MG 16444 and MG 16445 inhibit hypertriglyceridemia from ethanol resp. by 60.8% and 78.5% at the oral dosis of 0.37 mM/kg.

TABLE 5

| COMPOUND | DOSE mg/kg p.o. | Normolipemic rats % difference from control | | | |
|---|---|---|---|---|---|
| | | Chol. | TG | Chol-HDL | Liver Weight |
| MG 16311 | 0.37 × 4 days | −15.3 | −70.8 | +27.1 | −3.3 |
| MG 16426 | 0.37 × 4 days | −17.0 | −41.3 | +26.8 | +33.9 |
| MG 16448 | 0.37 × 4 days | −13.7 | −57.2 | +47.3 | +7.3 |
| MG 16444 | 0.185 × 4 days | −10.6 | −32.8 | +31.5 | −2.2 |
| MG 16444 | 0.37 × 4 days | −34.3 | −75.1 | +21.6 | +2.3 |
| MG 16445 | 0.092 × 4 days | −17.5 | −14.3 | +25.1 | −7.5 |
| MG 16445 | 0.185 × 4 days | −52.4 | −77.5 | −41.6 | +2.24 |

TABLE 5-continued

| COMPOUND | DOSE mg/kg p.o. | Normolipemic rats % difference from control | | | |
|---|---|---|---|---|---|
| | | Chol. | TG | Chol-HDL | Liver Weight |
| MG 16445 | 0.37 × 4 days | −44.7 | −67.5 | −19.0 | −5.2 |
| CLOFIBRATE | 0.82 × 4 days | −15.0 | −40.0 | 0 | +19.5 |
| PROBUCOL | 0.205 × 8 days | −25.0 | −28.0 | −26 | +4.0 |
| PROBUCOL | 0.82 × 4 days | ∼0 | ∼0 | +18.5 | 0 |

The anti-hypoxic activity was determined according to Yasuda et al., Arch. Int. Pharmacodyn. 233, 136, 1978.

Groups of 10 male mice (21–23 g) were treated orally with vehicle (controls) and the invention compounds. After 45 or 90 minutes the animals were decapitated and the gasping time was determined. Table 6 gives the results obtained after administration of some of the invention compounds which display an activity higher than Suloctidil.

TABLE 6

| COMPOUND | DOSE mg/kg/p.o. | Pretreatment time (min.) | Gasping time % diff. from control |
|---|---|---|---|
| MG 16288 | 100 | 45 | +50.2 |
| MG 16288 | 100 | 90 | +47.7 |
| MG 16318 | 100 | 45 | +38.7 |
| MG 16318 | 100 | 90 | +33.4 |
| MG 16311 | 100 | 45 | +45.6 |
| MG 16311 | 100 | 90 | +44.8 |
| MG 16310 | 100 | 45 | +51.0 |
| MG 16310 | 100 | 90 | +37.0 |
| MG 16444 | 50 | 90 | +38.4 |
| MG 16444 | 100 | 90 | +46.3 |
| FLUNARIZINE | 50 | 90 | +68.7 |
| SULOCTIDIL | 100 | 45 | +27.5 |
| SULOCTIDIL | 100 | 90 | +11.7 |

The oral acute toxicity in male mice of the invention compounds is very low. Thus, for example, the $LD_{50}$ is higher than 500 mg/kg for MG 16444 and MG 16445, higher than 1,000 mg/kg for MG 16426 and MG 16448, and higher than 2,000 mg/kg for MG 16302, MG 16294, MG 16287, MG 16310, MG 16313 and MG 16298.

The following are examples of manufacture of the compounds of the invention, but they are not to be intended as indicative of the limits of the scope of the same.

EXAMPLE 1 threo
1-(2,3-Dihydro-5-benzo-[b]-thienyl)-2-[4-(2-oxo-1-benzimidazolinyl)-1-piperidinyl]-propanol (MG 16270).

To a solution of 5.77 g (0.03 mole) of 5-propionyl-2,3-dihydrobenzo-[b]-thiophene (R. Usmanov et al., Dokl. Akad. Nauk Tadzh. SSR 18 11 1975) in 70 ml of anhydrous tetrahydrofuran (THF), 11.28 g (0.03 mole) of phenyl trimethyl ammonium tribromide is added at room temperature in small portions in about 5 hours under stirring. After additional 30 minutes of stirring at room temperature the mixture is poured into ice water made alkaline by the addition of $NaHCO_3$, extracted with diethyl ether and the organic phase is washed with water, dried over $MgSO_4$ and evaporated to dryness under reduced pressure. The residue is recrystallized from ligroin. Yield 5.7 g (70%); m.p. 79°–80° C.

NMR spectrum ($CDCl_3$): delta 1.88 (3H, d, $CHCH_3$); 3.35–3.43 (4H, m, dihydrotiophene ring); 5.24 (1H, q, $CHCH_3$); 7.28 (1H, d, aromatic); 7.78–7.82 (2H, m, aromatic).

To the above obtained 5-(alpha-bromopropionyl-2,3-dihydrobenzo[b]thiophene (7.4 g, 0.0273 mole) suspended in 100 ml of methanol, 5.4 g (0.0248 mole) of 4-(2-keto-1-benzimidazolinyl)-piperidine and 2.3 g of $NaHCO_3$ are added, and after refluxing for 16 hours with stirring the mixture is cooled to room temperature and 2 g (0.0526 mole) of $NaBH_4$ in 20 of water is dropped in 10 minutes into the mixture.

After additional heating for 4 hours under reflux, on cooling the mixture gives a precipitate which is collected, washed with methanol and recrystallized from a $DMF:H_2O$ 80:20 mixture. Yield 4.7 g (46%).

M.p. 259°–260° C.

Analysis for $C_{23}H_{27}N_3O_2S$ % calc.: C 67.45; H 6.65; N 10.26; S 7.83; found: C 67.31; H 6.75; N 10.36; S 7.74

The NMR spectrum ($CDCl_3:DMSO$ 3:1) gave the following values: $J_{CHOH/CHCH_3}$=10 Hz delta 0.8 (3H, d, $CHCH_3$); 1.86–3.08 (9H, $CH_2$ piperidine and $CHCH_3$); 3.29–3.35 (4H, m, $CH_2$ dihydrothiophene ring); 4.21 (1H, d, $CHOH$); 4.26 (1H, m, $CH_2$ piperidine); 5.0 (1H, s, $OH$); 7–7.23 (7H, m, aromatic); 10.68 (1H, s, $NH$).

EXAMPLE 2 threo
1-(2,3-Dihydro-2-methyl-5-benzo[b]thienyl)-2-[4-(2-oxo-1-benzimidazolinyl)-1-piperidinyl]-propanol (MG 16310).

Prepared by the same process used for the compound of Example 1, the starting compound being 2-methyl-5-propionyl-2,3-dihydrobenzo[b]thiophene (Usmanov et al., see above). The intermediate bromoderivative has m.p. 79°–81° C. (from hexane) and was obtained in 75% yield.

NMR ($CDCl_3$)=delta 1.46 (3H, d, $CHCH_3$ dihydrothiophene ring). The yield of the title compound was 48%; m.p. 220°–222° C. (from $DMF:H_2O$ 80:20).

Analysis for $C_{24}H_{29}N_3O_2S$ % calc.: C 68.05; H 6.90; N 9.92 S 7.57; found: C 67.95; H 6.80; N 10.01; S 7.45

NMR spectrum ($CDCl_3$) $J_{CHOH/CHCH_3}$=9.8 Hz delta 1.45 (3H, d, $CHCH_3$, dihydrothiophene ring)

EXAMPLE 3 threo
1-(6-Thiochromanyl)-2-[4-(2-oxo-1-benzimidazolinyl)-1-piperidinyl]-propanol (MG 16287).

Starting from 6-propionylthiochromane (Cagniant et al., Comptes Rendus Soc. Chim. France 223 1012, 1946), the alpha-bromoderivative is prepared by the process of Example 1 in 82% yield; m.p. 75°–77° C. (ligroin), NMR ($CDCl_3$) delta 2.09 (2H, q, $CH_2$ thiochromane ring). This is converted into 1-(6-thiochromanyl)-2-[4-(2-oxo-1-benzimidazolinyl)-1-piperidinyl]-propanone (MG 16290) as follows.

A mixture of 5 g of the bromoketone, 3.8 g of 4-(2-oxo-1-benzimidazolinyl)-piperidine and 1.77 g of triethylamine in 120 ml of ethanol is refluxed for 15 hours, cooled and poured into 600 ml of water. The precipitate is collected and recrystallized from methyl ethyl ketone.

Yield 3.7 (50%); m.p. 158°-160° C. NMR spectrum (CDCl$_3$): delta 2.16 (2H, m, CH$_2$ thiochromane ring).

The title compound is obtained by the process of Example 1 in 55% yield, m.p. 232°-235° C. (DMF:H$_2$O 80:20); J$_{C\underline{H}OH/CHC\underline{H}3}$=10 Hz structure confirmed by elemental analysis.

EXAMPLE 4 threo 1-(2-Methyl-6-thiochromanyl)-2-[4-(2-oxo-1-benzimidazolinyl)-1-piperidinyl]-propanol (MG 16311).

Starting from 2-methyl-6-propionylthiochromane (Lambelin et al., D.O.S. 2.651.572, C.A. 87 117766 s) the alpha-bromoderivative is prepared by the process of Example 1 in 65% yield; m.p. 82°-83° C. NMR spectrum (CDCl$_3$): delta 1.37 (3H, d, CHC$\underline{H}_3$ thiochromane ring). This is converted into 1-(2 methyl-6-thiochromanyl)-2-[4-(2-oxo-1-benzimidazolinyl)-1-piperidinyl]-propanone (MG 16318) as follows.

A mixture of 6.3 g of the bromoketone, 4.6. g of 4-(2-keto-1-benzimidazolinyl)-piperidine and 2.13 g of triethylamine in 180 ml of methanol is refluxed with stirring for 14 hours, cooled, poured into 1 liter of water and extracted with ethyl acetate. The residue obtained after evaporation of the organic solvent is recrystallized from benzene:ligroin 80:20.

Yield 3.3 g (36%), m.p. 160°-162° C. NMR spectrum (CDCl$_3$): delta 1.40 (3H, d, CHC$\underline{H}_3$ thiochromane ring).

The title compound is obtained by the process of Example 1 in 44% yield; m.p. 237°-239° C. (ethanol); J$_{C\underline{H}OH/CHC\underline{H}3}$=9.87 Hz; structure confirmed by elemental analysis.

EXAMPLE 5 threo and erythro 1-(2,3-Dihydro-5-benzo[b]thienyl)-2-[4-(2-oxo-1-benzimidazolinyl)-1-piperidinyl]-propanol (MG 16270 and MG 16295).

A suspension of 12.9 g (0.0476 mole) of 5-(alpha-bromopropionyl)-2,3-dihydrobenzo[b]thiophene (prepared as directed in Example 1) in 250 ml of methanol is treated with 9.4 g (0.0433 mole) of 4-(2-oxo-1-benzimidazolinyl)-piperidine and 3.5 g (0.0417 mole) of NaHCO$_3$ and heated to reflux for 15 hours. After cooling to room temperature, 3.5 g (0.0921 mole) of NaBH$_4$ in 35 ml of water is added slowly in about 1 hour, then the mixture is again refluxed for 6 hours. After cooling the mixture is diluted with water and extracted with CHCl$_3$, the organic phase is washed with water, dried and evaporated to dryness in vacuo. The residue, a mixture of the two diastereoisomers, is separated by dry column chromatography using silicagel 60 Merck 70-230 mesh and eluting with a chloroform: methanol 95:5 mixture.

The threo isomer is obtained in a 35% yield and analizes exactly like the identical compound of Example 1.

The erythro isomer is obtained in a 28% yield and has m.p. 201°-203° C. (ethanol).

The NMR spectrum shows (in DMSO) J$_{C\underline{H}OH/CHC\underline{H}3}$=5.49 Hz.

Analysis for C$_{23}$H$_{27}$N$_3$O$_0$S % calc.: C 67.45; H 6.65; N 10.26; S 7.83; found: C 67.39; H 6.61; N 10.15; S 7.82

EXAMPLES 6 TO 8

By using the same process as described in Example 5, and starting from the bromoketones obtained as intermediate compounds in Examples 2 to 4, a mixture of threo and erythro form of the invention compounds of Examples 2 to 4 is obtained and resolved into the individual stereoisomers.

The threo forms show the identical properties as the corresponding threo compounds prepared according to Example 2 to 4 and are obtained in yields of 33%, 30% and 31%, respectively. As to the erythro derivatives, they show the following properties. Yields are also given.

erythro 1-(2,3-Dihydro-2-methyl-5-benzo[b]thienyl)-2-[4-(2-oxo-1-piperidinyl)-propanol (MG 16357): m.p. 227°-228° C. (H$_2$O). Yield 20%.

erythro 1-(6-Thiochromanyl)-2-[4-(2-oxo-1-benzimidazolinyl)-1-piperidinyl]-propanol (MG 16299): m.p. 185°-186° C. (ethanol:water 80:20). Yield 27%.

erythro 1-(2-Methyl-6-thiochromanyl)-2-[4-(2-oxo-1-benzimidazolinyl)-1-piperidinyl]-propanol (MG 16317): m.p. 125°-130° C. (ethanol).

Yield 18%. J$_{C\underline{H}OH/CHC\underline{H}3}$=4 Hz

The elemental analysis and the NMR data confirmed the structure of the three compounds.

EXAMPLE 9

The threo-form of the compound of Example 1 (MG 16270) is prepared by the following alternative process.

A mixture of 7.4 g of 5-(alpha-bromopropionyl)-2,3-dihydrobenzo[b]thiophene (0.0273 mole) (see Example 1) and 100 ml of methanol is treated with 5.4 g of 4-(2-oxo-1-benzimidazolinyl)-piperidine (0.0248 mole) and 2.3 g of NaHCO$_3$ (0.0273 mole), then it is refluxed for 16 hours, cooled and poured into 400 ml of water.

The precipitate is collected and recrystallized from methyl ethyl ketone giving 5.6 g (55%) of 1-(2,3-dihydro-5-benzo[b]thienyl)-2-[4-(2-oxo-1-benzimidazolinyl)-1-piperidinyl]-propanone (MG 16278), m.p. 193°-195° C.

NMR (CDCl$_3$): delta 1.32 (3H, d, CHC$\underline{H}_3$); 1.81 (2H, m, CH$_2$ piperidine); 2.38-2.63 (4H, m, CH$_2$ piperidine); 2.97-3.12 (2H, m, CH$_2$ piperidine); 3.37-3.43 (4H, m, CH$_2$ dihydrothiophene); 4.15 (1H, q, C$\underline{H}$CH$_3$); 4.33 (1H, m, CH piperidine); 7.02-7.30 (5H, m, aromatic); 7.93-7.95 (2H, s, aromatic); 10.61 (1H, s, NH).

A solution of the foregoing ketone (3.71 g, 0.0091 mole) in 50 ml of THF is slowly dropped into a suspension of 0.720 g (0.019 mole) of LiAlH$_4$ in 10 ml of THF at 0° with stirring in a nitrogen atmosphere. The mixture is then stirred for additional 2 hours under N$_2$ at room temperature, treated with some water to destroy the excess reagent, diluted with water and extracted with chloroform. The organic phase gives on evaporation in vacuo a crude residue which is recrystallized from a DMF:H$_2$O 80:20 mixture.

Yield 1.86 g (50%), m.p. 259°-260° C.

EXAMPLE 10 threo and erythro 1-(2,3-Dihydro-5-benzo[b]thienyl)-2-[4-(1-oxo-3-phenyl-2-propenyl)-1-piperazinyl]-propanol (MG 16288 and MG 16298)

A mixture of 11.8 g (0.0435 mole) of 5-(alpha-bromopropionyl)-2,3-dihydrobenzo[b]thiophene (prepared as directed in Example 1) in 150 ml of methanol, 8.56 g (0.0396 mole) of 1-cinnamoylpiperazine and 3.3 g (0.0396 mole) of $NaHCO_3$ is refluxed with stirring for 17 hours, cooled to room temperature and quickly treated in 20 minutes with 3 g (0.0792 mole) of $NaBH_4$ in 30 ml of water. After refluxing for 4 hours the cooled mixture is poured into water and extracted with ethyl acetate. From the organic phase, on evaporation under reduced pressure, a solid is obtained which is chromatographed through silica gel using a mixture of chloroform:acetone 70:30 as the eluent.

The threo-isomer is obtained in 23% yield and has m.p. 141°–143° C. (ethanol). The yield of the erythro isomer is 41%; m.p. 139°–141° C. (ethanol).

Analysis for $C_{24}H_{28}N_2O_2S$ % calc.: C 70.55; H 6.91; N 6.86; S 7.85; threo: found: C 70.47; H 6.96; N 6.76; S 7.65; erythro: found: C 70.48; H 7.02; N 6.81; S 7.77

The NMR spectrum ($CDCl_3$) confirms the structures, in particular, it shows characteristic J values: threo: $J_{C\underline{H}OH/C\underline{H}CH_3}=9.87$ Hz; erythro: $J_{C\underline{H}OH/C\underline{H}CH_3}=4.02$ Hz

EXAMPLE 11 TO 21

By procedures substantially identical with that of Example 10, and starting from the appropriate bromoketone, the following compounds were prepared, of which the elemental analysis and the NMR data confirm the structure.

EXAMPLE 11

1-(2,3-Dihydro-2-methyl-5-benzo[b]thienyl)-2-[4-(1-oxo-3-phenyl-2-propenyl)-2-piperazinyl]-propanol threo: yield 37%, m.p. 160° C. (ethanol) $J_{C\underline{H}OH/C\underline{H}CH_3}=9.8$ Hz (MG 16351)
erythro: yield 25%, m.p. 150° C. (ethanol) $J_{C\underline{H}OH/C\underline{H}CH_3}=3.9$ Hz (MG 16358)

EXAMPLE 12

1-(6-Thiochromanyl)-2-[4-(1-oxo-3-phenyl-2-propenyl)-1-piperazinyl]-propanol threo: yield 25%, m.p. 143°–145° C. (ethanol) $J_{C\underline{H}OH/C\underline{H}CH_3}=9.87$ Hz (MG 16294)
erythro: yield 37%, m.p. 119°–120° C. (ethanol) $J_{C\underline{H}OH/C\underline{H}CH_3}=4.02$ Hz (MG 16302)

EXAMPLE 13

1-(2-Methyl-6-thiochromanyl)-2-[4-(1-oxo-3-phenyl-2-propenyl)-1-piperazynyl]-propanol threo: yield 25%, m.p. 154°–156° C. (ethanol) $J_{C\underline{H}OH/C\underline{H}CH_3}=9.87$ Hz (MG 16313)
erythro: yield 35%, m.p. 132°–136° C. (ethanol) $J_{C\underline{H}OH/C\underline{H}CH_3}=4.02$ Hz (MG 16315)

EXAMPLE 14

1-(2,3-Dihydro-5-benzo[b]thienyl)-2-[4-(1-oxo-3-(3,4,5-trimethoxyphenyl)-2-propenyl)-1-piperazinyl]-propanol threo: yield 20%, m.p. 176°–178° C. (ethanol) $J_{C\underline{H}OH/C\underline{H}CH_3}=9.87$ Hz (MG 16304)
erythro: yield 32%, m.p. 149°–151° C. (ethanol) $J_{C\underline{H}OH/C\underline{H}CH_3}=3.85$ Hz (MG 16308)

EXAMPLE 15

1-(2,3-Dihydro-2-methyl-5-benzo[b]thienyl)-2-[4-(1-oxo-3-(3,4,5-trimethoxyphenyl)-2-propenyl)-1-piperazinyl]-propanol threo: yield 21%, m.p. 138°–139° C. (ethanol) $J_{C\underline{H}OH/C\underline{H}CH_3}=10$ Hz (MG 16375)
erythro: yield 35%, m.p. 137°–138° C. (benzene:hexane 50:50) $J_{C\underline{H}OH/C\underline{H}CH_3}=3.8$ Hz (MG 16381)

EXAMPLE 16

1-(6-Thiochromanyl)-2-[4-(1-oxo-3-(3,4,5-trimethoxyphenyl)-2-propenyl)-1-piperazinyl]-propanol threo: yield 23%, m;p. 172°–174° C. (ethanol) $J_{C\underline{H}OH/C\underline{H}CH_3}=9.87$ Hz (MG 16305)
erythro: yield 25%, m.p; 137°–139° C. (ethanol) $J_{C\underline{H}OH/CH\underline{H}CH_3}=4.02$ Hz (MG 16309)

EXAMPLE 17

1-(2-Methyl-6-thiochromanyl)-2-[4-(1-oxo-3-(3,4,5-trimethoxyphenyl)-2-propenyl)-1-piperazinyl]-propanol threo: yield 33%, m.p. 150°–151° C. (ethanol) $J_{C\underline{H}OH/C\underline{H}CH_3}=9.87$ Hz (MG 16321)
erythro: yield 22%, m.p. 141°–143° C. (ethanol) $J_{C\underline{H}OH/C\underline{H}CH_3}=4$ Hz (MG 16323)

EXAMPLE 18

1-(2,3-Dihydro-5-benzo[b]thienyl)-2-]4-(2-furoyl)-1-piperazinyl]-propanol hydrochloride threo: yield 21%, m.p. 178°–182° C. (methyl ethyl ketone) $J_{C\underline{H}OH/C\underline{H}CH_3}=10.2$ Hz (MG 162969
erythro: yield 35%, m.p. 201°–204° C. (methanol) (MG 16307)

EXAMPLE 1)

1-(2,3-Dihydro-2-methyl-5-benzo[b]thienyl)-2-[4-(2-furoyl)-1-piperazinyl]-propanol hydrochloride threo: yield 35%, m.p. 199°–202° C. (isopropanol/diethyl ether) $J_{CHOH/CHCH_3}=9.8$ Hz (MG 16356)
erythro: yield 20%, m.p. 212°–213° C. (isopropanol/diethyl ether) (MG 16359)

EXAMPLE 20

1-(6-Thiochromanyl)-2-[4-(2-furoyl)-1-piperazinyl]-propanol hydrochloride threo: yield 30%, m.p. 192°–194° C. (isopropanol) $J_{C\underline{H}OH/C\underline{H}CH_3}=9.77$ Hz (MG 16300)
erythro: yield 20%, m.p. 220°–222° C. (methanol) (MG 16303)

EXAMPLE 21

1-(2-Methyl-6-thiochromanyl)-2-[4-(2-furoyl)-1-piperazinyl]-propanol threo: yield 33%, m.p. 136°–138° C. (ethanol) $J_{CHOH/CHCH_3}=9.87$ Hz (MG 16314)
erythro (oxalate): yield 15%, m.p. 155°–156° C. (isopropanol/diethyl ether) MG 16316).

EXAMPLE 22

The two stereoisomers of Example 12 are prepared by an alternate route which is described in the following.

A mixture of 6-(alpha-bromopropionyl)-thiochromane (prepared as described in Example 3) (8.7 g, 0.0277 mole), 6 g (0.0277 mole) of 1-cinnamoylpiperazine and 2.3 g (0.0277 mole) of NaHCO$_3$ in 200 ml of methanol is refluxed with stirring for 14 hours, cooled and treated at room temperature with 2.1 g (0.0534 mole) of NaBH$_4$ in small portions. After additional 5 hours of heating at reflux the cooled mixture is diluted with water and the precipitated solid is collected and recrystallized from ethanol. The erythro isomer is thus obtained in 35% yield; m.p. 119°–120° C.

The threo isomer is obtained in 20% yield by a single recrystallization of the residue obtained by evaporation of the mother liquor from the recrystallization of the erythro isomer and extracting with ethyl acetate and mother liquor of the reaction. M.p. 143°–145° C. (ethanol; water 70:30).

EXAMPLES 23 TO 28

By procedures substantially identical to that described in Example 10, and starting from 6-(alpha-bromopropionyl)-thiochromane prepared as teached in Example 1, the following compounds were prepared. Yields and melting points are given.

EXAMPLE 23

1-(6-Thiochromanyl)-2-[4-(1-oxo-3-(4-chlorophenyl)-2-propenyl)-1-piperazinyl]-propanol threo-isomer (MG 16403): 18%; m.p. 178°–179° C. (ethanol; $J_{C\underline{H}OH/C\underline{H}CH_3}$=9.5 Hz
erythro-isomer (MG 16409): 28%; m.p. 145°–146° C. (ethanol); $J_{C\underline{H}OH/C\underline{H}CH_3}$=4 Hz

EXAMPLE 24

1-(6-Thiochromanyl)-2-[4-(1-oxo-3-(3-chlorophenyl)-2-propenyl)-1-piperazinyl]-propanol threo-isomer (MG 16420): 14%; m.p. 155°–156° C. (ethanol); $J_{C\underline{H}OH/C\underline{H}CH_3}$=9.7 Hz
erythro-isomer (MG 16424): 20%; m.p. 116°–118° C. (ethanol); $J_{C\underline{H}OH/C\underline{H}CH_3}$=3.9 Hz

EXAMPLE 25

1-(6-Thiochromanyl)-2-[4-(1-oxo-3-(2-chlorophenyl)-2-propenyl)-1-piperazinyl]-propanol threo-isomer (MG 16421); 16%; m.p. 206°–209° C. (DMF:H$_2$O 80:20); $J_{C\underline{H}OH/C\underline{H}CH_3}$=9.7 Hz
erythro-isomer (MG 16425): 17%; m.p. 119°–123° C. (methylcellosolve:H$_2$O 75:25); $J_{C\underline{H}OH/C\underline{H}CH_3}$=4 Hz

EXAMPLE 26

1-6-Thiochromanyl)-2-[4-(1-oxo-3-(4-methoxyphenyl)-2-propenyl)-1-piperazinyl]-propanol threo-isomer (MG 16411): 24%, m.p. 144°–146° C. (ethanol); $J_{C\underline{H}OH/C\underline{H}CH_3}$=9.5 Hz
erythro-isomer (MG 16414): 22%; m.p. 171°–173° C. (ethanol); $J_{C\underline{H}OH/C\underline{H}CH_3}$=4 Hz

EXAMPLE 27

1-(6-Thiochromanyl)-2-[4-(1-oxo-3-(3-methoxyphenyl)-2-propenyl)-1-piperazinyl]-propanol threo-isomer (MG 16427): 23%; m.p. 140°–141° C. (ethanol); $J_{C\underline{H}OH/C\underline{H}CH_3}$=10 Hz
erytro-isomer (MG 16430): 22%; m.p. 125°–126° C. (ethanol); $J_{C\underline{H}OH/C\underline{H}CH_3}$=4 Hz

EXAMPLE 28

1-(6-Thiochromanyl)-2-[4-(1-oxo-3-(2-methoxyphenyl)-2-propenyl)-1-piperazinyl]-propanol threo-isomer (MG 16428): 20%; m.p. 133°–135° C. (ethanol); $J_{C\underline{H}OH/C\underline{H}CH_3}$=10 Hz
erythro-isomer (hydrogen oxalate) (MG 16431): 7%; m.p. 126°–130° C. (ethanol);

EXAMPLE 29

1-(6-Thiochromanyl)-2-[4-(1-oxo-3-phenyl-2-propenyl)-1-piperazinyl]-ethanol (MG 16426)

Into a solution of 5 g of 6-acetylthiochromane (Foley et al., J. Chem. Soc. 1963, 1899) in 10 ml of chloroform 1.3 ml of bromine is dropped at 5° C. and the mixture is stirred for 3 hrs. After addition of a 5% aqueous solution of NaHCO$_3$ the organic layer is separated, dried and evaporated to dryness. Yield 5.5 g (78%) of 6-(alpha-bromoacetyl)-thiochromane (MG 16406), m.p. 92°–94° C. (ligroine), which is then reacted with 1-cinnamoylpiperazine and then reduced with NaBH$_4$ according to Example 10.

Yield 37%; m.p. 181°–183° C. (DMF:H$_2$O 80:20).

EXAMPLE 30

1-(6-Thiochromanyl)-2-[4-(2-oxo-1-benzimidazolinyl)-1-piperidinyl]-ethanol (MG 16410)

By the procedure of Example 29, and starting from 6-(alpha-bromoacetyl)-thiochromane and 4-(2-oxo-1-benzimidazolinyl)-piperidine, the corresponding aminoketone is obtained in 38% yield (MG 16413), m.p. 184°–186° C., which is then reduced with NaBH$_4$.

Yield 42%, m.p. 162°–163° C. (ethyl acetate).

EXAMPLE 31

1-(6-Thiochromanyl)-2-[4-(2-oxo-5-chloro-1-benzimidazolinyl)-1-piperidinyl]-propanol threo-isomer (MG 16443): 19%; m.p. 278°–281° C. (methylcellosolve); $J_{C\underline{H}OH/C\underline{H}CH_3}$=9.5 Hz
erythro-isomer (MG 16446): 12%; m.p. 191°–194° C. (ethanol); $J_{C\underline{H}OH/C\underline{H}CH_3}$=4 Hz The intermediate aminoketone (MG 16448; m.p. 187°–191° C.) is prepared from 6-(alpha-bromopropionyl)-thiochromane (in turn prepared according to the procedure of Example 29 for the bromoacetyl homologue) and 4-(2-oxo-5-chloro-1-benzimidazolinyl)-piperidine.

EXAMPLE 32 threo-1-(6-Thiochromanyl)-2-[4-(2-methyl-1-benzimidazolinyl)-1-piperidinyl]-propanol (MG 16477)

43% m.p; 168°–170° C.; $J_{C\underline{H}OH/C\underline{H}CH_3}$=9.8 Hz
The intermediate aminoketone (MG 16457, m.p. 158°–160° C. with dec., as hydrogen oxalate) is prepared from 6-(alpha-bromopropionyl)thiochromane and 4-(2-methyl-1-benzymidazolinyl)-piperidine.

EXAMPLE 33

1-(6-Thiochromanyl)-2-(4-benzamido-1-piperidinyl)-propanol threo-isomer (MG 16444): 46%; m.p. 206°–208° C. (methylcellosolve), $J_{C\underline{H}OH/C\underline{H}CH_3}$=9.5 Hz
erythro-isomer (MG 16445): 8%; m.p. 200°–201° C. (ethanol): $J_{C\underline{H}OH/C\underline{H}CH_3}$=3.8 Hz.

EXAMPLE 34 threo-1-(6-Thiochromanyl)-2-[4-(2-oxo-3-indolinyl)-1-piperidinylidenyl]-propanol (MG 16458)

4%; m.p. 209°–211° C. (methylcellosolve); $J_{\underline{CH}OH/\underline{CH}CH_3} = 9.6$ Hz The intermediate aminoketone (MG 16449; m.p. 177°–179° C.) is prepared as in the foregoing Examples starting from 3-(4-piperidinylidene)-indolin-2-one. The following hydrogenation was carried out with diisobutyl aluminum hydride at −20° C. in $CH_2Cl_2$ under nitrogen.

EXAMPLE 35

1-(6-Thiochromanyl)-2-[4-(1-oxo-3-phenyl-2-propenyl)-1-piperazinyl]-butanol

Prepared from 1-cinnamoylpiperazine and 6-(alpha-bromobutanoyl)-thiochromane (MG 16467), in turn prepared by bromination of 6-butanoylthiochromane and obtained as an oil sufficiently pure for the subsequent step.

threo-isomer (MG 16473): 35%; m.p. 171°–172° C. (ethanol); $J_{\underline{CH}OH/\underline{CH}CH_3} = 9.5$ Hz erythro-isomer (MG 16474): 7%; m.p. 150°–151° C. (ethanol); $J_{\underline{CH}OH/\underline{CH}CH_3} = 4$ Hz

EXAMPLE 36

1-(6-Thiochromanyl)-2-[4-(1-oxo-3-phenyl-2-propenyl-1-piperazinyl]-pentanol threo-isomer (MG 16469): 25%; m.p. 168°–169° C. (ethanol); $J_{\underline{CH}OH/CCH_3} = 9.5$ Hz erythro-isomer (MG 16471): 22%; m.p. 167°–168° C. (ethanol); $J_{\underline{CH}OH/\underline{CH}CH_3} = 4$ Hz The intermediate aminoketone is prepared starting from 6-pentanoylthiochromane (Cagniant et al., C.R. Soc. Chim. France 223, 1012, 1946) through the alpha-bromoderivative and condensation with 1-cinnamoylpiperazine.

EXAMPLE 37

1-(6-Thiochromanyl)-2-(1-piperazinyl)-propanol

A mixture of 10 g of 6-(alpha-bromopropionyl)-thiochromane, 4 g of N-formylpiperazine and 3 g of $NaHCO_3$ in 200 ml of ethanol is stirred at the boiling temperature for 8 hrs, then 2.6 g of $NaBH_4$ in 30 ml of water is added and heating is continued for 4 hrs. After cooling and dilution with water the mixture is extracted with ethyl acetate. A mixture of the stereoisomers of 1-(6-thiochromanyl)-2-[4-(1-formyl)-piperazinyl]-ethanol (MG 16475) is obtained. After separation of the stereoisomers on $SiO_2$ with $CHCl_3:CH_3OH$ 97.5:2.5, they are hydrolized with ethanolic NaOH.

threo-isomer (MG 16476) dihydrochloride: 19%; m.p. 241°–243° C.; $J_{CHOH/CCH_3} = 9.5$ Hz erythro-isomer (MG 16484) dihydrochloride: 26%; m.p. 236°–239° C.

EXAMPLE 38

1-(6-Thiochromanyl)-2-[4-(2-oxo-1-benzimidazolinyl-methyl)-1-piperidinyl]-propanol threo-isomer (MG 16486): 38%; m.p. 217°–220° C.; $J_{CHOH/CHCH_3} = 9.8$ Hz erythro-isomer (MG 16492): 23%, m.p. 190°–192° C.; $J_{CHOH/CHCH_3} = 4$ Hz

EXAMPLE 39

1-(6-Thiochromanyl)-2-[4-(1-oxo-3-(2-thienyl)-2-propenyl)-1-piperazinyl]-propanol threo-isomer (MG 16494); 20%; m.p. 173°–174° C. (ethanol) (oxalate)

erythro-isomer (MG 16496); 40%; m.p. 206°–208° C. (ethanbol) (oxalate)

EXAMPLE 40

-(6-Thiochromanyl)-2-[4-(1-oxo-3-(2-furyl)-2-propenyl)-1-piperazinyl]-propanol threo-isomer (MG 16493): 43%; m.p. 176°–177° C. (i-propanol) (oxalate)

erythro-isomer (MG 16495): 44%; m.p. 196°–197° C. (ethanol) (oxalate)

EXAMPLE 41

1-(6-Thiochromanyl)-2-[4-(1-oxo-3-phenyl-2-propenyl)-1-piperazinyl]-propanone (MG 16477)

Prepared as the hydrochloride from 6-(alpha-bromopropionyl)-thiochromane and 1-cinnamoylpiperazine. Yield 47%; m.p. 221°–224° C. (ethanol). The NMR spectrum confirms structure.

We claim:

1. A compound of the formula

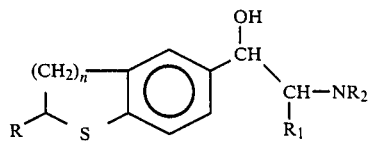

in its cis and trans configuration and mixtures thereof, wherein R and $R_1$ represent hydrogen or a lower alkyl group, n represents an integer selected from 1 and 2, and $R_2$ represents a divalent radical selected from (a)

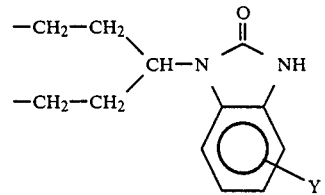

wherein Y represents hydrogen or halogen;

(b)

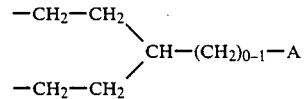

wherein A is a group selected from

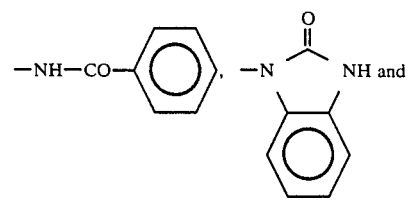

-continued

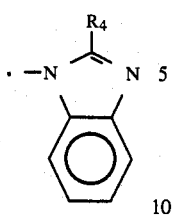

wherein R₄ represents a lower alkyl group;

(c)

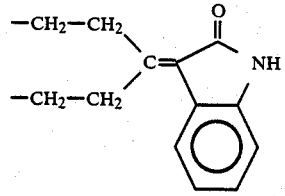

and (d)

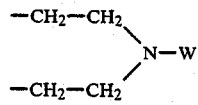

wherein W represents a 2-furoyl radical or a group

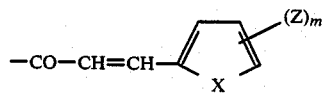

wherein X represents a group selected from —CH=CH—, —O— and —S—, Z represents a hydrogen, halogen or a lower alkyl or alkoxy group and m is an integer from 1 to 3, and their salts with inorganic acids, organic acids, or cationic exchange resins and complexes with cyclodextrins.

2. A compound of the formula

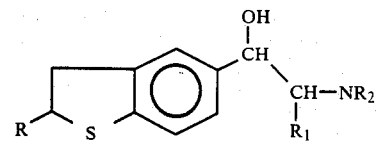

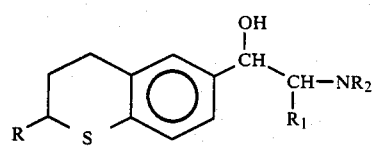

in its cis- and trans-configuration and mixtures thereof, wherein R, R₁ and R₂ have the same significance as in claim 1, and its salts with inorganic and organic acids.

3. A compound of the formula in its cis- and trans-configuration and mixtures thereof, wherein R, R₁ and R₂ have the same significance as in claim 1, and its salts with inorganic and organic acids.

4. A compound selected from the stereoisomeric threo and erythro form of 1-(6-thiochromanyl)-2-[4-(1-oxo-3-phenyl-2-propenyl)-1-piperazinyl]-propanol and their mixtures.

5. A compound selected from the stereoisomeric threo and erythro form of 1-(6-thiochromanyl)-2-(4-benzamido-1-piperdinyl)-propanol and their mixtures.

6. A compound selected from the stereoisomeric threo and erythro form of 1-(6-thiochromanyl)-2-[4-(oxo-1-benzimidazolinyl)-1-piperidinyl]-propanol and their mixtures.

7. A compound selected from the stereoisomeric threo and erythro form of 1-(2,3-dihydro-5-benzo[b]-thienyl-2-[4-(1-oxo-3-phenyl-2-propenyl)-1-piperazinyl]-propanol and their mixtures.

8. A compound selected from the stereoisomeric threo and erythro form of 1-(2-methyl-6-thiochromanyl)-2-[4-(1-oxo-3-phenyl)-1-piperazinyl]-propanol.

9. A compound of the formula:

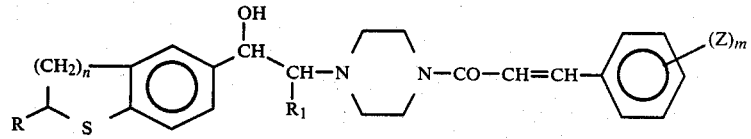

wherein Z is hydrogen, halogen, lower alkyl or lower alkoxy, R and R₁ represent hydrogen or a lower alkyl group, m is an integer from 1 to 3 and n is 1 or 2, salts of said compound with inorganic acids, organic acids or cationic exchange resins and complexes of said compound with cyclodextrins.

* * * * *